United States Patent [19]

Harvey et al.

[11] 4,425,322
[45] Jan. 10, 1984

[54] DUAL-ACTION DENTIFRICE

[75] Inventors: Kenneth Harvey, Wilmslow; Harry Hayes, Warrington, both of England

[73] Assignee: Colgate-Palmolive Company, New York, N.Y.

[21] Appl. No.: 386,361

[22] Filed: Jun. 8, 1982

[30] Foreign Application Priority Data

Jun. 11, 1981 [GB] United Kingdom ............... 8117907

[51] Int. Cl.$^3$ .................... A61K 7/16; A61K 7/18
[52] U.S. Cl. .................................... 424/52; 424/49
[58] Field of Search ........................................ 424/52

[56] References Cited

U.S. PATENT DOCUMENTS

| 2,818,371 | 12/1957 | Wessinger | 424/52 |
|---|---|---|---|
| 3,070,510 | 12/1962 | Cooley et al. | 424/52 |
| 3,175,731 | 3/1965 | Ellman | 424/52 |
| 3,711,604 | 1/1973 | Cocodney et al. | 424/52 |
| 3,728,446 | 4/1973 | Roberts et al. | 424/52 |
| 3,881,529 | 5/1975 | Mannara | 141/100 |
| 3,885,028 | 5/1975 | Cella et al. | 424/52 |
| 3,919,409 | 11/1975 | Perla et al. | 424/52 |
| 3,929,987 | 12/1975 | Colodney et al. | 424/52 |
| 3,966,863 | 6/1976 | Forward et al. | 424/52 |
| 3,980,767 | 9/1976 | Chown et al. | 424/52 |
| 4,042,680 | 8/1977 | Muhler et al. | 424/55 |
| 4,069,311 | 1/1978 | Mannara | 424/52 |
| 4,069,312 | 1/1978 | Mannara | 424/52 |
| 4,108,979 | 8/1978 | Muhler et al. | 424/52 |
| 4,108,981 | 8/1978 | Muhler et al. | 424/52 |
| 4,132,771 | 1/1979 | Schreiber et al. | 424/52 |
| 4,169,885 | 10/1979 | Raaf et al. | 424/52 |
| 4,196,189 | 4/1980 | Raaf et al. | 424/52 |
| 4,203,966 | 5/1980 | Faunce | 424/52 |
| 4,292,304 | 9/1981 | Barels et al. | 424/52 |
| 4,328,205 | 5/1982 | Taylor | 424/52 |
| 4,348,378 | 9/1982 | Kosti | 424/52 |
| 4,358,437 | 11/1982 | Duke | 424/52 |

FOREIGN PATENT DOCUMENTS

| 813514 | 5/1959 | United Kingdom . | |
| 962757 | 7/1964 | United Kingdom . | |
| 1271944 | 4/1972 | United Kingdom . | |
| 1492660 | 11/1977 | United Kingdom . | |
| 1408922 | 10/1975 | United Kingdom | 424/52 |

OTHER PUBLICATIONS

Gerhardt et al., J. Dent. Res. 51:870 (1972) Fluoride Uptake in Natural Tooth Surfaces Pretreated with Aluminium Nitrate.
McCann, "Archives of Oral Biology", vol. 14, 1969, p. 521-531.

Primary Examiner—Shep K. Rose
Attorney, Agent, or Firm—Robert L. Stone; Murray M. Grill; Herbert S. Sylvester

[57] ABSTRACT

A dentifrice is described comprising an aqueous phase containing aluminium and an oil phase containing fluoride, the immiscibility and physiochemical properties of the phases resulting in a "dual action" effect on dentition to which this dentifrice is applied by substantially separate treatment with aluminium and then fluoride.

18 Claims, No Drawings

DUAL-ACTION DENTIFRICE

This invention relates to dentifrices, more particularly to dentifrices having a "dual action" effect as described below.

It is known from in vitro studies described in McCann, "The Effect of Fluoride Complex Formation on Fluoride Uptake and Retention in Human Enamel", Archives of Oral Biology, Vol. 14 (1969), Page 521 and Gerhardt et al, "Fluoride Uptake in Natural Tooth Surfaces Pretreated with Aluminium Nitrate", Journal of Dental Research, Vol. 51 (1972), Page 870, that enamel pretreated with aluminium compound solution followed by treatment with a fluoride solution substantially increases fluoride effectiveness over the use of aluminium and fluoride at the same time this being an example of a "dual effect" process, the aluminium pretreatment comprising the one stage and the following fluoride treatment providing the other stage of the duality.

It has been suggested, for instance in U.S. Pat. Nos. 4,042,680: 4,108,979; and 4,108,981, each to Muhler et al, to use aluminium compounds in dentifrices which may contain fluoride compounds. In U.S. Pat. Nos. 4,042,680 and 4,108,981 complexes of aluminium are preformed or formed in situ in the dentifrice. In U.S. Pat. No. 4,108,979, water soluble aluminium compound is employed. In U.S. Pat. No. 3,728,446 to Roberts et al, aluminium salt is insolubilized with formation of visible particles of aluminium carboxymethylcellulose in a dentifrice, which dentifrice may contain a fluoride.

The prior art has not however taught an effective technique for providing a single dentifrice product which can be mixed, without resorting to distinct functional particles suspended in a dentifrice vehicle, (such particles requiring specialized manufacturing techniques which can be complex), the dentifrice having a "dual action" effect wherein the benefits of separate two stage aluminium and fluoride treatment can be obtained.

In accordance with one aspect of the present invention a dentifrice comprises;

an aqueous humectant phase I comprising a water-soluble aluminium salt in amount to provide the dentifrice with a non-toxic amount of aluminium ions, the aluminium salt being dispersed in a vehicle comprising about 10–95% by weight of phase I of water and humectant and 0.25–10% by weight of phase I of gelling agent;

and an oil phase II comprising a fluorine-providing compound in amount to provide the dentifrice with an effective anticariogenic non-toxic amount of fluorine corresponding to about 100 to about 10,000 ppm fluoride ions, the fluorine providing compound being dispersed in a vehicle comprising about 20–85% by weight of phase II of a non-toxic oil substantially immiscible with phase I;

wherein the surface tensions of the two phases produce a sufficiently large interfacial tension to maintain immiscibility; phase I and phase II being present in a weight ratio of about 50:1 to 0.6:1; and at least one of phase I and phase II comprising a dentally acceptable water-insoluble polishing agent in amount of about 20–75% by weight of the dentifrice.

It is an advantage of this invention that a dual-action effect can be obtained wherein dentifrice enamel can be first treated with aluminium and then with fluoride.

Further advantages are that improved reduction in enamel solubility and increased uptake of fluoride may be obtained.

Other advantages will be apparent from the following description.

Phase I of the dentifrice comprises water and humectant as liquid carrying material for the water soluble aluminium salt. Typically, water and humectant comprise about 20–95% by weight of phase I, preferably about 25%–55%. Water typically comprises about 20–60% by weight of the liquid carrying material and humectant the remainder. Among humectants which may be employed are glycerine, sorbitol (typically 70% solution), low molecular weight (e.g. about 400–600) polyethylene glycol, propylene glycol, mannitol and other sugar alcohols, polyoxyethylene glycols and mixtures thereof.

It is desirable to provide phase I with a creamy or liquid consistency by including in the phase a gelling or binding agent. Desirably, this agent is compatible with the water-soluble aluminium salt and does not react therewith to form a precipitate. Such gelling agents include hydroxyalkyl cellulose such as hydroxymethyl cellulose, hydroxyethyl cellulose and hydroxypropyl cellulose, viscarin, gelatin, starch, glucose, sucrose, polyvinyl pyrollidone, polyvinyl alcohol, gum tragacanth, gum karaya, methyl cellulose, and synthetic colloidal magnesium silicate clays such as are available under the trademarks LAPONITE and BENTONE. Hydroxyalkyl cellulose, particularly hydroxyethyl cellulose, is preferred. The gelling agent typically comprises about 0.25–5% by weight of phase I, preferably about 0.5–2%.

The particular water-soluble aluminium salt employed in phase I is not critical, and substantially any non-toxic, water-soluble aluminium ion containing salt or hydrate thereof may be used. Suitable aluminium salts include aluminium sulphate (e.g. $Al_2(SO_4)_3.16H_2O$ and $Al_3(SO_4)_3.14H_2O$), aluminium potassium sulphate (e.g. $AlK\text{-}(SO_4)_2.12H_2O$), aluminium chloride (e.g. $AlCl_3.6H_2O$), aluminium sodium sulphate (e.g. $AlNa(SO_4)_2.12H_2O$), aluminium ammonium sulphate (e.g. $AlNH_4(SO_4)_2.12H_2O$), aluminium sodium phosphate (e.g. $NaAl_3H_4(PO_4)_8.4H_2O$), aluminium nitrate (e.g. $Al(NO_3)_3.\text{-}9(H_2O)$) and sodium aluminate ($NaAl(OH)_4$). Mixtures of such salts and/or hydrates may be used. Aluminium sulphate, aluminium monovalent metal sulphate and aluminium chloride are preferred.

The aluminium salt is present in phase I in an amount to provide the dentifrice with a non-toxic amount of aluminium corresponding to about 10 ppm to about 50,000 ppm aluminium ions (about 0.001–5.0% by weight), preferably about 25 ppm to about 10,000 ppm (about 0.0025–1%), most preferably about 100 ppm to about 4,000 ppm (about 0.01–0.4%). Thus, in the case of $Al_2(SO_4)_3.16H_2O$, about 0.026% by weight in the dentifrice provide about 25 ppm of aluminium.

The dentifrice typically contains a dentally acceptable polishing agent in one or both of the phases. The polishing material in phase I (if present) is desirably compatible with the water-soluble aluminium salt, so as to result in minimal precipitation of aluminium compounds. Such polishing materials include hydrated alumina, anhydrous alumina, kaolin abrasives such as are described and incorporated in U.S. Pat. Nos. 4,042,680; 4,108,979; and 4,108,981 zirconium silicate, calcined and uncalcined talcs ($Mg_3Si_4O_{10}(OH)_2$), barium sulphate calcined aluminium silicate; resin abrasives such as are described in U.S. Pat. No. 3,070,510, and siliceous polishing materials such as sodium aluminosilicate, silica containing combined alumina, silica xerogel and precipitated silica. Mixtures of such materials may be employed. When polishing material is employed in phase I, it typically comprises about 10–75% by weight of the phase, and preferably about 25–60% if polishing material is present in both phases.

Various other materials which are substantially non-reactive with the aluminium ion containing salt may be incorporated into phase I. Examples thereof include preservatives, such as $C_1$–$C_4$ alkyl benzyl esters of p-hydroxybenzoic acid, astringents, such as pyridyl carbinol, coagulants such as allantoin, surface active agents such as sodium lauryl sulphate, sodium N-lauroyl sarcosinate and phosphate mono- and di-ester mixtures available under the trademark BEROL, which are anionic in nature, and condensates of sorbitan monostearate with approximately 20 moles of ethylene oxide and condensates of ethylene oxide with propylene oxide, which are nonionic in character, silicones, chlorophyll compounds, ammoniated materials, such as urea, diammonium phosphate and mixtures thereof, and colour materials. These adjuvants are incorporated in phase I in amounts which do not adversely affect the properties and characteristics and are suitably selected and used in proper amounts depending upon the particular type of preparation. For instance, the surface active agent is generally about 0.05–10% by weight, preferably about 0.5–5%, of phase I.

Any flavourings or sweetening sialogogue may be employed in phase I which is appropriate and suitable. Examples include the flavouring oils, such as oils of spearmint, peppermint, wintergreen, sassafras, clove, sage, eucalyptus, marjoram, cinnamon, lemon and orange, as well as methylsalicylate. Sweeteners include sucrose, lactose, maltose, sorbitol, saccharin and sodium cyclamate. The sialogogue components may comprise about 0.01–5% by weight or more of phase I.

Phase II is an oil phase in which a fluorine-providing compound is maintained separate from the water-soluble aluminium salt of phase I. The fluorine-providing compound has a beneficial effect on the care and hygiene of the oral cavity, e.g. diminution of enamel solubility in acid and protection of the teeth against decay. In accordance with this invention this effect is increased in the dentifrice composition by effecting contact of the teeth with the aluminium salt prior to contact with the fluorine-providing-compound by placing the fluorine-providing compound in a phase form which it emerges more slowly than does the aluminium from its separate phase due to the different physiochemical properties of the two phases. In particular, the surface tension of phase II is lower than that of phase I and the interfacial tension between the two surfaces results in immiscibility of the two phases. Examples of suitable fluorine-providing compounds include sodium fluoride, stannous fluoride, potassium fluoride, potassium stannous fluoride ($Sn_nF_2$.KF) stannous chlorofluoride, sodium monofluorophosphate, sodium fluorozirconate, potassium fluorozirconate, stannous fluorozirconate, indium fluorozirconate and complex zirconium-germanium fluorides (e.g. $Zr(GeF_6)_2$, $ZrGeF_8$, $Ge(ZrF_6)_2$ and $ZrOGeF_6$).

Other suitable fluorine-providing compounds include ammonium fluoride, indium fluoride, ferrous fluoride, lithium fluoride, fluorosilicates, such as $Na_2SiF_6$, calcium fluorozirconates, fluorostannites, such as $NaSnF_3$, fluoroborates, such as $NaBF_4$, fluorotitanates, such as $NaTiF_5$ and mixed tin fluorohalides, such as $SnClF$ and $Sn_2ClF_6$. Mixtures of fluorine providing compounds may be used. The preferred fluorine-providing compounds are sodium fluoride and sodium monofluorophosphate or mixtures thereof, with sodium fluoride being most preferred. These compounds are used in effective non-toxic amounts, such as about 0.01–1% by weight, based on the water-soluble fluorine content. For instance, this corresponds to about 0.02–2% by weight of sodium fluoride and about 0.08–8% by weight of sodium monofluorophosphate. The preferred water-soluble fluorine content range is about 0.1–0.5% by weight (about 1,000 ppm to about 5,000 ppm).

Suitable non-toxic oils for use in the vehicle of phase II include those which have viscosity in the range from 100 to 300 centipoises at 21° C. and can be mineral oil, light petrolatum thickened to an appropriate viscosity or vegetable oils. Such oils are described in British Pat. No. 1,492,660, the disclosure of which is incorporated herein by reference. Similar bland potable animal oils, such as triolein, may be used too.

The preferred mineral oil is Mineral Oil U.S.P. (also known as Liquid Petrolatum U.S.P., mineral oil (heavy medicinal), white mineral oil, liquid paraffin and heavy liquid petrolatum). Mineral Oil U.S.P. is defined in Remington's Pharmaceutical Sciences, 13th Edition, Mack Publishing Co., Easton, Pa. 1965, U.S.A., as a mixture of liquid hydrocarbons obtained from petroleum; a colourless, transparent, oily liquid, free or nearly free from fluorescene. It is tasteless and odourless when cold and develops not more than a faint odour of petroleum when heated. Its specific gravity is between 0.860 and 0.905, and its kinematic viscosity is not less than 38.1 centistokes at 37.8° C. (i.e. not less than 32.8 centipoises at 37.8° C.). A particularly preferred oil is Mineral Oil U.S.P. having a viscosity of about 250 centipoises at 21.1° C., sold under the trade name PENTOL.

The preferred light liquid petrolatum is Light Liquid Petrolatum N.F. also known as light liquid paraffin and light white mineral oil. It is described in Remington's Pharmaceutical Sciences, as " . . . a mixture of liquid hydrocarbons obtained from petroleum. It may contain a stabilizer." The specific gravity is given as between 0.828 and 0.880; and the kinematic viscosity is given as not more than 37 centistokes at 37.8° C. (or not more than 32.6 centipoises at 37.8° C.). If the Light Liquid Petrolatum N.F. is used as the oil it should be preferably thickened to the required viscosity of from about 100 to about 300 centipoises at 21.1° C. with a thickener, such as one of the well-known commercially available inert thickening materials, e.g., a pyrogenic silica sold under the trade mark CABOSIL; or a hydrogenated castor oil, sold under the trade name THIXIN.

Suitable vegetable oils include coconut oil, cottonseed oil, sesame oil and similar non-toxic vegetable oils, as described in Vegetable Fats and Oils, by E. W. Eckey, Reinhold Publishing Corp., New York, U.S.A., 1954. The vegetable oil selected should fall within the said viscosity range of from 100 to 300 centipoises at 21.1° C. A particular vegetable oil falling within this range is "Neobee M-5", a fractioned triglyceride of coconut oil. It is desirable that the vegetable oil ingredient contain a minor amount of an antioxidant such as butylated hydroxyanisole or butylated hydroxytoluene, preferably in an amount in the range from 0.1% to 3% by weight, based on the weight of the vegetable oil employed. Low molecular weight polyethylene glycol may be used with oil in phase II.

The oil ingredient may be employed in amounts in the range from about 20% to 80 or 85%, preferably 50% to about 85% by weight, of phase II.

The oil of phase II is desirably gelled and thickened with a gelling agent and or a thickener, to provide a creamy or gel consistency to the phase. Gelling agents such as those described from phase I may be employed. Alternatively, other gelling agents may be employed, such as alkali metal carboxyalkyl cellulose (e.g. sodium carboxymethylcellulose) and polyethylenes such as is available as AC 6 under the trade mark POLYTHENE. The preferred gelling agents for phase II are the polyethylenes and the clays such as LAPONITE and BENTONE. Thickeners include pyrogenic silica, such as M-5 under the trade mark CABOSIL, 244 and 266 under the trade mark SYLOID and D-200 under the trade mark AEROSIL, silica aerogel, alumina fines or other similar low density finely divided powers. The gelling agent typically amounts to up to about 10% by weight of phase II, preferably about 3–7%. The thickener typically amounts to about 1–35% by weight of phase II, preferably about 1–5%.

Phase II may contain a dentally acceptable polishing agent in amounts compatible with the fluorine-providing compound. Polishing agents described for phase I may also be used in phase II. In addition, other polishing agents which may be used in phase II include alkaline earth metal phosphates, such as dicalcium phosphate (dihydrate and anhydrous), tricalcium phosphate, calcium pyrophosphate and dimagnesium phosphate as well as insoluble sodium metaphosphate calcium carbonate and sodium bicarbonate. Mixtures of polishing agents may be employed. As indicated, any particular polishing agent is used in amount which is compatible with the fluorine providing compound. The preferred polishing system for phase II is a siliceous polishing material such as available under the trade mark ZEO as ZEO 49, a silicon dioxide with low combined alumina (or a sodium aluminium silicate) optionally with a minor amount of calcium carbonate. The polishing agent desirably comprises up to about 50% by weight of phase II, typically about 5–45%, preferably about 20–40%.

Phase II may also contain other materials which may be present in phase I such as preservatives, astringents, surface active agents, silicones, chlorophyll compounds, ammoniated materials, colour materials and sialogogues, in similar amounts to those given above for phase I. Such agents should be compatbile with the fluorine providing compound. Sodium benzoate may be used as a preservative. The surface active agent may be anionic, nonionic, cationic or ampholytic. Bacteriostatic compounds may be employed in amount up to about 5% by weight of phase II.

A gel of mineral oil and Polyethylene "AC 6" (Allied Chemical, U.S.A.) is prepared by either shock cooling or by cold grinding in a colloid mill. One method of shock cooling is to dissolve the polyethylene in two-thirds of the formula amount of hot mineral oil (100° C.), allowing this to cool to just above the cloudpoint of the mixture (88° C.), and then adding the remaining one-third of chilled (0° C.) mineral oil and stirring vigorously. Alternatively, the hot solution of polyethylene in all the formula amount of mineral oil may be shock cooled on a rotating chill roller. If prepared by the cold grinding method, the polyethylene is milled with the mineral oil in a colloid mill vibroreactor until a suitable gel dispersion is obtained.

The gel is then transferred to a vacuum mixing vessel and the remaining ingredients of phase II are added and mixed until homogeneous and air free.

The two phases may be incorporated into an extrudible dentifrice and packaged into a container or tube of lined aluminium, lined lead or plastic, side-by-side, since there is little tendency for them to become miscible. However, more desirably they are incorporated into separate compartments of a tube having dividers which permits simultaneous extrusion. The two phase ribbons can be extruded simultaneously for common application to a toothbrush and simultaneous brushing on the teeth since differences in the physiochemical properties between the non-aqueous oil phase II and the aqueous phase I permits the aluminium content of phase I to reach the teeth earlier than the fluoride content of phase II.

The phases are present in a weight ratio of I:II of about 50:1 to 0.6:1, preferably about 30:1 to 1:1. When the weight ratio of I:II is about 30:1 or more a tube of the type described in British Pat. No. 813,514 to Marraffino may be employed and the extruded dentifrice has an appearance in which phase I is a stripe. When the ratio of I:II is about 1:1 or less, filling nozzles and tubes of the type described in British Pat. No. 962,757 to Evans may be employed and the phases appear as one enveloping the other. Other techniques which may be employed to divide phases while permitting simultaneous extrusion are described in U.S. Pat. No. 4,098,435, to Weyn, British Pat. No. 1,271,944 to Chown et al and British Pat. No. 1,418,695 to Colgate-Palmolive.

The following specific Examples are further illustrative of the present invention. The amounts and proportions of the compositions described in the Examples are by weight unless otherwise specified.

EXAMPLE 1

The following two-phase dentifrice is prepared:

| I AQUEOUS PHASE | | II OIL PHASE | |
|---|---|---|---|
| COMPONENTS | PARTS | COMPONENTS | |
| Sorbitol (70%) | 23.00 | Mineral Oil (heavy) | 54.66 |
| Hydroxyethyl cellulose | 1.10 | Polyethylene (POLYTHENE AC 6) | 5.34 |
| Sodium saccharin | 0.20 | Flavour | 1.14 |
| Aluminium sulphate hexadecahydrate | 1.46 | Sodium lauryl sulphate L100 | 2.61 |
| Allantoin | 0.15 | Polyethylene glycol 600 | 3.86 |
| Water | 19.13 | Silicon dioxide with combined alumina (ZEO 49) | 29.55 |
| Hydrated alumina (ALCOA C-333)* | 52.00 | Silica thickener (SYLOID 244) | 1.82 |
| Sodium Lauryl sulphate (LZV) | 1.76 | Titanium dioxide | 0.45 |
| Flavour | 1.20 | Sodium fluoride | 0.57 |

*ALCOA is a trademark.

Phase I is prepared by gelling the humectant system with the hydroxyethyl cellulose and minor ingredients followed by the addition of the abrasive and then the surfactant and flavouring. The phase is homogenised and deaerated under vacuum.

Phase II is prepared by shock cooling the mineral oil/polyethylene mixture to form a gel followed by the addition of abrasives, sodium fluoride, and other ingredients. The phase is homogenised by mixing and deareated under vacuum.

The phases are filled into a dentifrice tube with phase I supplied through a filling nozzle and phase II supplied through a conduit as described in British Pat. No. 962,757. Phases I and II are employed in a weight ratio of 2:1. The complete dentifrice thus contains 780 ppm of aluminium and 1425 ppm of fluoride. (The phases have sufficiently high interfacial tension so as to keep the active ingredients separate even when the two phases are homogeneously mixed in the same container.)

Upon extrusion of a dentifrice ribbon from the tube onto a toothbrush followed by brushing onto dental enamel, the aluminium from phase I is released more quickly than the fluoride from Phase II. Reduction of enamel solubility and increase of fluoride uptake by enamel is greater with this two-phase dentifrice than with a dentifrice formulated according to phase I but also including sodium fluoride in amount providing 1425 ppm fluoride in place of a corresponding portion of water.

Similar improved results are obtained by using 1.97 parts of sodium monofluorophosphate in phase II in place of the sodium fluoride to provide 1425 ppm fluoride to the dentifrice.

EXAMPLE 2

The following two-phase dentifrice is prepared:

| I AQUEOUS PHASE | | II OIL PHASE | |
|---|---|---|---|
| COMPONENTS | PARTS | COMPONENTS | PARTS |
| Sorbitol (70%) | 23.00 | Mineral Oil (Heavy) | 81.90 |
| Hydroxyethyl cellulose | 1.10 | Polyethylene (AC6) | 4.70 |
| Sodium saccharin | 0.20 | Polyethylene glycol 600 | 3.40 |
| Aluminium sulphate hexadecahydrate | 0.73 | Sodium fluoride | 10.00 |
| Allantoin | 0.15 | | |
| Water | 19.86 | | |
| Hydrated alumina (ALCOA C-333) | 52.00 | | |
| Sodium lauryl sulphate (LZV) | 1.76 | | |
| Flavour | 1.20 | | |

The phases are prepared in a manner similar to that described in Example 1, with the preparation technique for the phase II particularly modified in view of the fewer components used.

The phases are filled into a dentifrice tube with divided sections for each of the phases as described in British Pat. No. 813,514. Phases I and II are employed in a weight ratio of 30:1. The complete dentifrice thus contains 780 ppm of aluminium and 1515 ppm of fluoride. (The phases have sufficiently high interfacial tension so as to keep the active ingredients separate even when the two phases are mixed in the same container.)

Upon extrusion of a dentifrice ribbon from the tube onto a toothbrush followed by brushing onto teeth, the aluminium from phase I is released more quickly than the fluoride from phase II. Reduction of enamel solubility and increase of fluoride uptake by enamel is greater with this two-phase dentifrice than with a dentifrice according to phase I but also including sodium fluoride in amount providing 1515 ppm fluoride in place of a corresponding portion of water.

We claim:
1. A dentifrice comprising;
an aqueous humectant phase I comprising a water-soluble aluminium salt in amount to provide the dentifrice with a non-toxic amount of aluminium ions, the aluminium salt being dispersed in a vehicle comprising about 10-95% by weight of phase I of water and humectant and 0.25-10% by weight of phase I of gelling agent;
and an oil phase II comprising a fluorine-providing compound in amount to provide the dentifrice with an effective anticariogenic non-toxic amount of fluorine corresponding to about 100 to about 10,000 ppm fluoride ions, the fluorine providing compound being dispersed in a vehicle comprising about 20-85% by weight of phase II of a non-toxic oil substantially immiscible with phase I;
wherein the surface tensions of the two phases produce a sufficiently large interfacial tension to maintain immiscibility; phase I and phase II being present in a weight ratio of about 50:1 to 0.6:1; and at least of one of phase I and phase II comprising a dentally acceptable water-insoluble polishing agent in amount of about 20-75% by weight of the dentifrice.

2. The dentifrice as claimed in claim 1 wherein the water and humectant comprise about 20-95% by weight of phase I.

3. The dentifrice as claimed in claim 1 wherein the water and humectant comprise about 25-55% by weight of phase I.

4. The dentifrice as claimed in claim 1 wherein the water comprises about 20-60% by weight of phase I.

5. The dentifrice as claimed in claim 1 wherein the gelling agent comprises about 0.25-5% by weight of phase I.

6. The dentifrice as claimed in claim 5 wherein the gelling agent comprises about 0.5-2% by weight of phase I.

7. The dentifrice as claimed in claim 1 wherein the aluminium ions are provided by aluminium sulphate, aluminium monovalent metal sulphate or aluminium chloride, or hydrates thereof, or a mixture of such salts and/or hydrates.

8. The dentifrice as claimed in claim 7 comprising aluminium ions in amount of about 25 ppm to about 10,000 ppm by weight.

9. The dentifrice as claimed in claim 8 comprising aluminium ions in amount of about 100 ppm to about 4,000 ppm by weight.

10. The dentifrice claimed in claim 1 wherein the non-toxic oil of phase II is a blend potable oil which is mineral oil, thickened light petrolatum, vegetable oils or animal oils, or a mixture thereof.

11. The dentifrice claimed in claim 1 wherein said oil is present in amount of about 50-85% by weight of phase II.

12. The dentifrice as claimed in claim 1 wherein the fluoride ions are provided to phase II by sodium fluoride, sodium monofluorophosphate or a mixture thereof.

13. The dentifrice claimed in claim 12 comprising fluoride ions in amount of about 1,000 ppm to about 5,000 ppm by weight.

14. The dentifrice as claimed in claim 1 wherein the dentally acceptable water-insoluble polishing agent is present at least in phase I in an amount of about 10-75% by weight of phase I.

15. The dentifrice as claimed in claim 14 wherein the polishing agent is hydrated alumina.

16. The dentifrice as claimed in claim 14 wherein polishing agent is present in each of phase I and phase II, and is present in amount of about 25–60% by weight of phase I and up to about 50% by weight of phase II.

17. The dentifrice as claimed in claim 16 wherein the polishing agent present in phase I is hydrated alumina and the polishing agent present in phase II is a siliceous polishing material.

18. A process for dual action application to dentition which comprises applying to dentition the dentifrice claimed in claim 1 thereby pretreating dentition with the aluminium content of phase I followed by treatment of the dentition with the fluoride content of phase II.

* * * * *